United States Patent
Ho et al.

(10) Patent No.: US 7,862,744 B2
(45) Date of Patent: Jan. 4, 2011

(54) METHODS AND SYSTEMS FOR PREPARING MATERIALS FOR SUCRALOSE PRODUCTION

(75) Inventors: David Losan Ho, Los Angeles, CA (US); Zhenghao Wan, Wyuishan (CN)

(73) Assignee: Mamtek International Limited, Hong Kong (HK)

( * ) Notice: Subject to any disclaimer, the term of this patent is extended or adjusted under 35 U.S.C. 154(b) by 5 days.

(21) Appl. No.: 12/178,527

(22) Filed: Jul. 23, 2008

(65) Prior Publication Data
US 2010/0019195 A1  Jan. 28, 2010

(51) Int. Cl.
| | |
|---|---|
| C09K 3/00 | (2006.01) |
| C07H 17/02 | (2006.01) |
| C07H 1/00 | (2006.01) |
| C07H 1/06 | (2006.01) |
| B01D 11/00 | (2006.01) |
| B01D 21/01 | (2006.01) |
| B01D 37/00 | (2006.01) |

(52) U.S. Cl. ............... 252/182.12; 536/17.2; 536/124; 536/127; 210/634; 210/734; 210/767; 210/770
(58) Field of Classification Search ............ 252/182.12; 536/122, 127, 124, 17.2; 564/137; 210/634, 210/734, 767, 770
See application file for complete search history.

(56) References Cited

U.S. PATENT DOCUMENTS 3,072,725 A * 1/1963 Surman ............... 564/137

FOREIGN PATENT DOCUMENTS

JP       03148244    *  6/1991

* cited by examiner

*Primary Examiner*—Ling-Siu Choi
*Assistant Examiner*—Monique Peets
(74) *Attorney, Agent, or Firm*—Perkins Coie LLP

(57) ABSTRACT

The present invention provides a method for preparing DMF for sucralose production, including, e.g., isolating DMF from a composition comprising DMF, water, and methanol, using a single-tower rectification system. In various embodiments of the present invention, the composition, after the removal of water and methanol, may be further dried/dehydrated, such as, by using a dehydration agent and/or filtration. The resulting substantially pure DMF may comprise at least about 98-99% DMF. The present invention further provides a method of preparing a composition comprising anhydrous sucrose for sucralose production, which may comprise mixing regular sucrose with a water-containing DMF composition, and drying the resulting sucrose-DMF composition. Also provided is a single-tower separation system for isolating DMF from a composition comprising DMF, water, and methanol.

12 Claims, 1 Drawing Sheet

US 7,862,744 B2

METHODS AND SYSTEMS FOR PREPARING MATERIALS FOR SUCRALOSE PRODUCTION

FIELD OF THE INVENTION

The present invention relates generally to methods and systems for preparing materials, such as, N,N-dimethylformamide (hereinafter, "DMF"), and anhydrous sucrose, for use in the production of sucralose.

BACKGROUND OF THE INVENTION

The artificial sweetener 4,1', 6'-trichloro-4,1', 6'-trideoxygalactosucrose ("sucralose") is derived from sucrose by replacing the hydroxyls in the 4, 1', and 6' positions with chlorine. A number of different synthesis routes for the preparation of sucralose have been developed in which the reactive hydroxyl in the 6 position is first blocked, as by an ester group, prior to the chlorination of the hydroxyls in the 4, 1', and 6' positions, followed by hydrolysis to remove the ester substituent to produce sucralose. Several of these synthesis routes involve tin-mediated synthesis of sucrose-6-esters.

Sucrose-6-esters may be chlorinated, such as, by the process of Walkup et al. (U.S. Pat. No. 4,980,463, which is incorporated herein by reference in its entirety). The chlorination process produces as a product a sucralose-6-ester, such as 4,1',6'-trichloro-4, 1',6'-trideoxygalactosucrose-6-acetate, in solution in a tertiary amide, typically DMF, plus salts (produced as a result of neutralizing the chlorinating agent after completion of the chlorination reaction), chlorination reaction byproducts, and other impurities. Exemplary chlorination reaction byproducts include chlorinated carbohydrates other than sucralose, such as mono- and di-chlorinated sucrose, as well as other forms of chlorinated sucrose.

Conventionally, after a neutralization step, a raw material for sucralose production, i.e., the tertiary amide reaction vehicle (e.g., DMF) for the chlorination reaction, as well as liquid waste/byproduct of the sucralose production process, may be removed, such as, by steam distillation. Such waste composition may contain DMF (e.g., about 45-50%), methanol (e.g., about 25-30%), water (e.g., about 20-25%), and other organic and/or inorganic compositions. Traditionally, DMF is recovered and recycled from the waste liquid using a multi-tower distillation system, which is capable of purifying DMF up to 99.95% pure and has a recovery rate up to 80%. The recovered DMF may be re-used in sucralose production. However, such multi-tower distillation systems occupy a large area and expensive to use.

Another raw material for sucralose production is sucrose. Since the existent of water interferes with the chlorination process, sucralose manufacture requires the use of anhydrous sucrose, which may be obtained by purchasing high grade anhydrous sucrose from a commercial supplier or drying ordinary sucrose under vacuum condition. However, neither option is optimal because: (1) anhydrous sucrose is very expensive (about 30% higher than the best ordinary first grade sucrose); and (2) the vacuum drying is costly, time-consuming, and labor intensive.

Therefore, there exists a need for effective, efficient, and economical methods and systems for preparing raw materials (e.g., DMF and anhydrous sucrose) used in sucralose production.

SUMMARY OF THE INVENTION

Briefly described, in its preferred form, the present invention provides a method for isolating DMF from a composition comprising DMF, water, and methanol, which may comprise: introducing a composition comprising DMF, water, and methanol into a separation system; isolating DMF from the composition, wherein the isolated DMF is substantially free of water and methanol; and drying the isolated DMF, whereby a substantially pure DMF is produced. In one embodiment, the separation system is a single-tower separation system. In another embodiment, the single-tower separation system comprises a lower section and an upper section, and the composition comprising DMF, water, and methanol is introduced into the lower section.

In various embodiments, the composition comprising DMF, water, and methanol is heated, e.g., by using steam, to remove methanol and water, and to rectify DMF from the waste composition. In one embodiment, water and methanol may be removed by using the following steps: decreasing the pressure of the separation system by using a vacuum system; maintaining the temperatures of the lower section of the single-tower separation system at about 25-45° C., whereby methanol may be substantially removed from the composition; and maintaining the temperatures of the lower section at about 45-75° C., whereby water may be substantially removed from the composition. In another embodiment, DMF may be rectified by decreasing the pressure of the separation system by using a vacuum system; and maintaining the temperatures of the lower section of the single-tower separation system at about 60-95° C. for a period sufficient to separate DMF from the impurities in the waste composition. In yet another embodiment, the temperature of the upper section of the single-tower separation system may be about 5-10° C. lower than that of the temperatures of the lower section. In various embodiments of the present invention, the operating pressure of the separation system may be a pressure of about −0.07 MPa to about −0.099 MPa.

The rectified DMF may be further dried/dehydrated, such as, by using a dehydration agent and/or filtration. The resulting substantially pure DMF may comprise at least about 98% DMF or at least about 99% DMF.

The present invention also provides a method for isolating DMF from a composition comprising DMF, water, and methanol, which may comprise: providing a single-tower separation system comprises a lower section and an upper section; introducing a composition comprising DMF, water, and methanol into the lower section of the single-tower separation system; decreasing the pressure of the separation system by using a vacuum system; maintaining the temperatures of the lower section at about 25-45° C., whereby methanol may be substantially removed from the composition; maintaining the temperatures of the lower section at about 45-75° C., whereby water may be substantially removed from the composition; maintaining the temperatures of the lower section of the single-tower separation system at about 60-95° C., whereby DMF may be substantially removed and recovered from the composition; and drying the rectified DMF (e.g., by using a dehydration agent), whereby a substantially pure DMF composition may be produced.

The present invention further provides a method of preparing a composition containing anhydrous sucrose, which comprises: applying a sucrose composition to a DMF composition, whereby a sucrose-DMF composition may be produced, and wherein both the sucrose composition and the DMF composition comprise water; and drying the sucrose-DMF composition, thereby producing the composition containing anhydrous sucrose.

Also provided is a single-tower separation system for isolating DMF from a composition comprising DMF, water, and methanol, wherein: the single-tower separation system comprises an inlet, an outlet, a lower section/chamber, an upper section/chamber, and optionally, a cooling system, and a storage container/tank; the inlet allows the introduction of the composition comprising DMF, water, and methanol into the lower section of the single-tower separation system; the outlet allows the removal of water and methanol, as well as the collection of the recovered DMF; and the cooling system allows the cooling of vaporized or gaseous water, methanol, and DMF to their liquid form.

Other features and advantages of the present invention will become apparent from the following detailed description. It should be understood, however, that the detailed description and the specific examples, while indicating the preferred embodiments of the present invention, are given by way of illustration only, since various changes and modifications within the spirit and scope of the present invention will become apparent to those skilled in the art from this detailed description.

BRIEF DESCRIPTION OF THE DRAWING

These and other objects and features of this invention will be better understood from the following detailed description taken in conjunction with the drawing wherein.

DETAILED DESCRIPTION OF THE PREFERRED EMBODIMENTS

Figure 1:
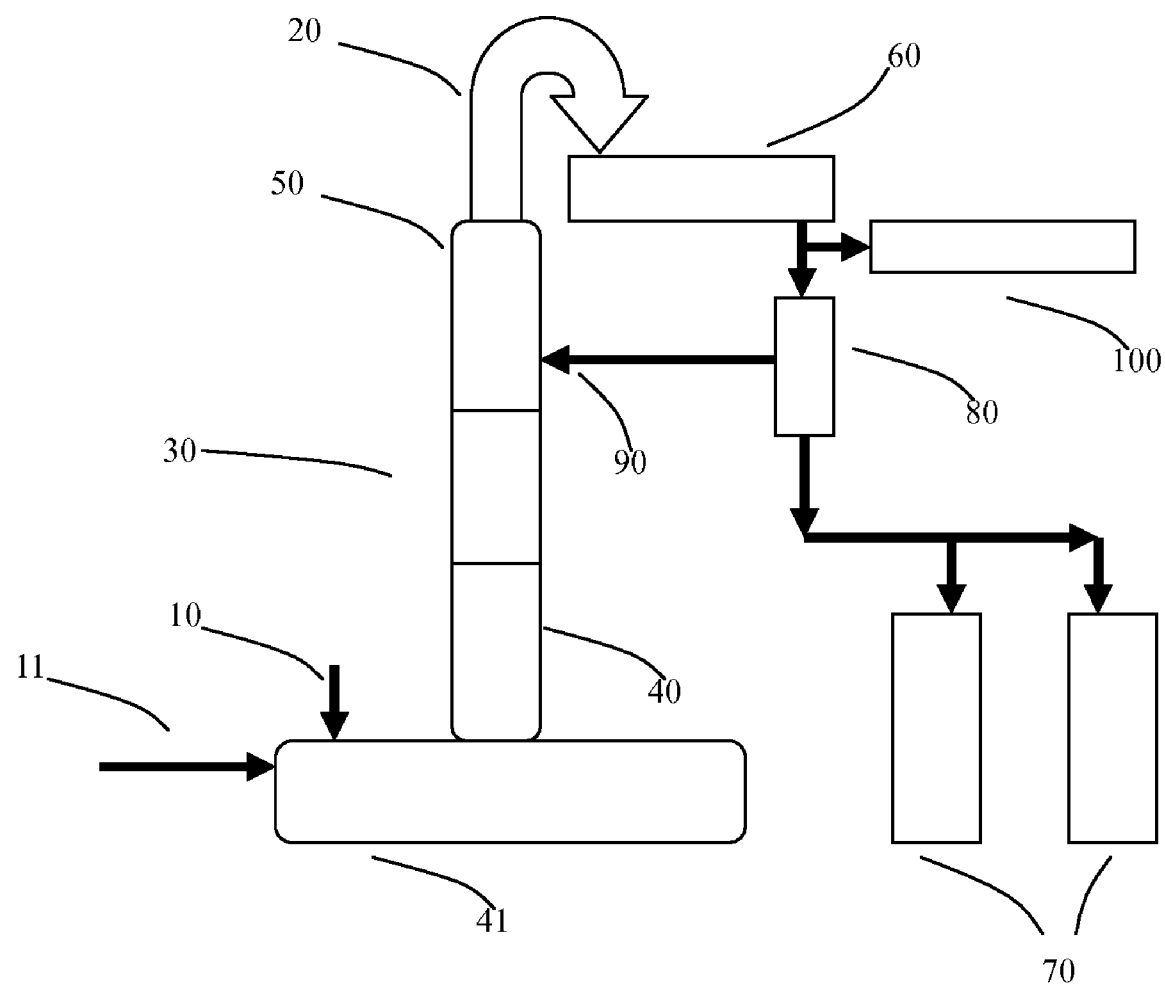
FIG. 1 illustrates a representative embodiment of the present invention, wherein the FIGURE is simplified for clarity.

The present invention pertains to methods and systems for preparing materials, such as, DMF and anhydrous sucrose, for sucralose production, wherein the methods and systems of the present invention utilize the differences in the boiling points of methanol, water, and DMF, i.e., methanol may be removed from waste liquid at a relatively low temperature which is sufficient to evaporate methanol but insufficient to evaporate water and DMF, while water may be removed from the waste liquid at a temperature sufficient to evaporate water but insufficient to evaporate DMF. A DMF recycling system based on the technology of the present invention has drastically reduced requirements for equipment investment (e.g., such that the investment requirement is about 10% of the multi-tower distillation system currently known in the art) and the space. The DMF recycling system of the present invention is also easier to operate, compared to a multi-tower distillation system.

The present invention also provides methods for preparing a composition containing anhydrous sucrose, which include removing moisture from ordinary sucrose (e.g., ordinary first grade sucrose). The resulting sucrose may have a water content of less than, e.g., about 0.3%, which is suitable for sucralose manufacturing purposes.

In one aspect, the present invention provides a method for isolating DMF from a composition comprising DMF, water, and methanol, which may comprise: introducing a composition comprising DMF, water, and methanol into a separation system; isolating DMF from the composition, wherein the isolated DMF is substantially free of water and methanol; and drying the isolated DMF, whereby a substantially pure DMF may be produced. The composition comprising DMF, water, and methanol may include, without limitation, any composition containing DMF, water, and methanol, such as, waste liquid resulting from sucralose production. Methods for producing sucralose are known in the art, see, e.g., U.S. patent application Ser. Nos. 11/552,789 and 11/552,813, the content of which is incorporated by reference herein in its entirety.

In various embodiments of the present invention, the separation system is a single-tower separation system. As illustrated in FIG. 1, the single-tower separation system may comprise one or a plurality of inlets (10 and 11), one or a plurality of outlets 20, a rectification chamber 30 comprising a lower section/chamber 40 (including a feed plate 41) and an upper section/chamber 50, and optionally, a cooling system 60, one or more storage containers/tanks 70, a separating unit 80, a feedback conduit 90, and a vacuum system 100.

The inlet allows the introduction of the composition comprising DMF, water, and methanol to the lower section 40 of the single-tower separation system. In one embodiment, the single-tower separation system may contain a second inlet 11 for introducing steam into the rectification chamber.

The outlet allows the removal of water, methanol, and other impurities from the rectification chamber, as well as the collection of the recovered DMF for the rectification chamber. In one embodiment, the single-tower separation system may comprise one outlet, which may be functionally/operationally linked to the upper section 50 and may be used for releasing gaseous water, methanol, and/or DMF from the rectification chamber 30. In another embodiment, the single-tower separation system may contain a second outlet, which may be functionally/operationally linked to the lower section 40 and may be used for releasing impurities from the rectification chamber 30. In yet another embodiment, the inlet 10 or 11 may be used as an outlet for releasing impurities from the rectification chamber 30. In still another embodiment, the single-tower separation system may contain a steam outlet for releasing steam.

The rectification chamber 30 may contain a plurality of identical, similar, or different sections. In some embodiments, each section or a number of selected sections of the rectification chamber 30 may include structures to facilitate the rectification process, such as, structures/fillers made of stainless steel. Such structures/means (e.g., without limitation, a layered structure, or a net/mesh structure) are well known in the art. In various embodiments, the rectification chamber 30 may have a length/height of about 10-32 meters, about 12-28 meters, about 16-24 meters, or about 20 meters.

The cooling system allows the cooling of vaporized or gaseous water, methanol, and/or DMF to its liquid form. Any cooling system known in the art suitable for the purposes of the present invention may be used. In one embodiment, the cooling system may be a passive cooling system, wherein the gaseous water or methanol may be cooled by exposing it to the environment. In another embodiment, the cooling system may be an active cooling system, which enables the contact of gaseous water or methanol with cold and/or running cooling media, such as, without limitation, cold water, cold salt water, or air. The term "contact," as used herein, includes direct contact and indirect contact, such as, without limitation, an indirect contact via a heat-exchanging material (e.g., through a metal tubing), or a direct contact with cooling air or water.

In various embodiments of the present invention, the composition comprising DMF, water, and methanol may be introduced into the lower section of the rectification chamber. Thereafter, the composition comprising DMF, water, and methanol may be heated, e.g., by using steam, to remove methanol and water. Any heating methods known in the art suitable for the purposes of the present invention may be used. Exemplary heating methods/systems may include, without limitation, heating with steam, a burner, an electric heating device, and a microwave-based heating device.

In one embodiment, water and methanol may be removed by using the following steps: reducing the pressure of the rectification chamber by using a vacuum system; maintaining the temperatures of the lower section of the single-tower separation system at about 25-45° C., whereby methanol may be substantially removed from the composition; and maintaining the temperatures of the lower section at about 45-75° C., whereby water may be substantially removed from the composition. Other operating temperatures may also be used. For example, in some embodiments, for removing methanol from the composition, the temperatures of the lower section may be maintained at about 30° C.-40° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., about 40° C., about 41° C., about 42° C., about 43° C., about 44° C., or about 45° C. In another embodiment, for removing water from the composition, the temperatures of the lower section may be maintained at about 50° C.-65° C., about 46° C., about 47° C., about 48° C., about 49° C., about 50° C., about 51° C., about 52° C., about 53° C., about 54° C., about 55° C., about 56° C., about 57° C., about 58° C., about 59° C., about 60° C., about 61° C., about 62° C., about 63° C., about 64° C., about 65° C., about 66° C., about 67° C., about 68° C., about 69° C., about 70° C., about 71° C., about 72° C., about 73° C., about 74° C., or about 75° C. In addition, a person skilled in the art would understand that the temperatures suitable for the purposes of the present invention may vary as a result of the changes in the pressure. For example, a higher temperature may be needed to obtain a desired result at a higher pressure, while a lower temperature may be used to obtained the same or similar result at a lower pressure.

In various embodiments, the temperature of the upper section of the single-tower separation system may be about 5-10° C. lower than that of the temperatures of the lower section. Methods for controlling the temperature of the upper section are known in the art, such as, by adjusting the heat input into the separation system (e.g., amount/flow rate of the steam), the pressure of the rectification chamber, and/or the height of the rectification chamber.

In one embodiment, after the removal of water and methanol, DMF may be recovered by using the following steps: reducing the pressure of the rectification chamber by using a vacuum system; maintaining the temperatures of the lower section of the single-tower separation system at about 60-95° C., whereby DMF may be substantially removed from the composition, leaving impurities in the waste composition. Other operating temperatures may also be used. For example, in some embodiments, for recovering DMF from the composition, the temperatures of the lower section may be maintained at about 65° C.-90° C., about 70° C.-85° C., about 75° C.-80° C., about 60° C., about 61° C., about 62° C., about 63° C., about 64° C., about 65° C., about 66° C., about 67° C., about 68° C., about 69° C., about 70° C., about 71° C., about 72° C., about 73° C., about 74° C., about 75° C., about 76° C., about 77° C., about 78° C., about 79° C., about 80° C., about 81° C., about 82° C., about 83° C., about 84° C., about 85° C., about 86° C., about 87° C., about 88° C., about 89° C., about 90° C., about 91° C., about 92° C., about 93° C., about 94° C., or about 95° C.

Methods and systems for decreasing the pressure of the rectification chamber are known in the art. In some embodiment, one or more vacuum machine 100 may be operationally connected with the separation system of the present invention. In one embodiment, a vacuum machine may be connected at a position downstream of the cooling system. In another embodiment, a vacuum machine may be connected to the storage tank. A person skilled in the art would understand that changing the pressure of the system may affect the temperatures suitable for the purposes of the present invention. For example, a higher temperature may be needed to obtain a desired result when the system is operated at a higher pressure, while a lower temperature may be used to obtain the same or similar result when the system is operated at a lower pressure.

In various embodiments of the present invention, the separating unit 80 may be controlled to direct liquid water, methanol, or DMF to return to the rectification chamber 30 through the feedback conduit 90 for further rectification. For example, water may be rectified at about 45-75° C. for about 30-60 minutes and the cooled, liquid water passes through the separating unit 80 and is stored in the storage container/tank 70, wherein the water is substantially free of DMF. The separating unit 80 is then adjusted to direct the liquid water, which may contain a higher level of DMF, to return to the rectification chamber 30 through the feedback conduit 90 for further rectification for 30-60 minutes, such that, the resulting liquid water becomes substantially DMF-free. Thereafter, the separating unit 80 is re-adjusted to direct the liquid water to flow to the storage container/tank 70.

In various embodiments of the present invention, the rectified DMF may be further dried/dehydrated, such as, by using a dehydration agent and/or filtration. Any method for drying a liquid known in the art suitable for the purposes of the present invention may be used, which may include, without limitation, vacuum drying, heating, reverse osmosis, filtering, and dehydration using a dehydration agent. Dehydration agents suitable for the purposes of the present invention are known in the art, such as, without limitation, silica gel, quicklime, unslaked lime, gypsum, sodium sulfate, magnesium sulfate, calcium sulfate, calcium chloride, calcium oxide, montmorillonite clay, and molecular sieves. The resulting substantially pure DMF may comprise at least about 98% DMF or at least about 99% DMF. In one embodiment, the DMF may be at least about 99.5% pure.

The present invention also provides a method for isolating DMF from a composition comprising DMF, water, and methanol, which may comprise: providing a single-tower separation system comprises a lower section and an upper section; introducing a composition comprising DMF, water, and methanol into the lower section of the single-tower separation system; decreasing the pressure of the separation system by using a vacuum system; maintaining the temperatures of the lower section at about 25-45° C., whereby methanol may be substantially removed from the composition; maintaining the temperatures of the lower section at about 45-75° C., whereby water may be substantially removed from the composition; maintaining the temperatures of the lower section of the single-tower separation system at about 60-95° C., whereby DMF may be substantially removed and recovered from the composition; and drying the composition, whereby a substantially pure DMF composition may be produced (e.g., by using a dehydration agent).

The present invention further provides a method of preparing a composition containing anhydrous sucrose, which comprises: applying a sucrose composition to a DMF composition, whereby a sucrose-DMF composition may be produced, and wherein both the sucrose composition and the DMF composition comprise water; and drying the sucrose-DMF composition. The term "sucrose composition," as used herein, includes, without limitation, any sucrose suitable for use in sucralose production (e.g., sucrose containing more than about 1% water; ordinary first grade sucrose). Sucrose composition may also contain non-sucrose substance, compound, or composition, such as, other substrates of the sucralose synthesis. The term "DMF composition," as used herein, includes, without limitation, any water-containing DMF composition suitable for the purposes of the present invention (e.g., the semi-purified DMF composition collected from the single-tower separation system of the present invention).

Sucralose manufacture requires anhydrous sucrose, which generally may be obtained by purchasing high grade anhydrous sucrose from a commercial supplier or by drying ordinary sucrose (which contains water, such as, 1-2% water) under vacuum condition. However, neither option is optimal. For example, anhydrous sucrose is very expensive (e.g., about 30% higher than ordinary first grade sucrose). In addition, the vacuum drying is costly, time-consuming, and labor intensive.

In various embodiments of the present invention, ordinary sucrose, such as commercially available ordinary first grade sucrose, may be mixed with or dissolved in a water-containing DMF composition, such as, the DMF composition collected from the single-tower separation system, which typically has about 1-3% of water. The sucrose-DMF mixture or solution may then undergo a drying and/or a filtration step to remove water from the mixture/solution. Any methods for drying a liquid known in the art suitable for the purposes of the present invention may be used, which may include, without limitation, filtering, and dehydration using a dehydration agent. Filtering and/or dehydration agents suitable for the purposes of the present invention are known in the art, such as, without limitation, silica gel, quicklime, unslaked lime, gypsum, sodium sulfate, magnesium sulfate, calcium sulfate, calcium chloride, calcium oxide, montmorillonite clay, and molecular sieves. In some embodiments, the resulting sucrose may have a water content of less than about 0.9%, about 0.7%, about 0.5%, or about 0.3%, which is suitable for sucralose manufacturing purposes.

The present invention is described in the following Examples, which are set forth to aid in the understanding of the invention, and should not be construed to limit in any way the scope of the invention as defined in the claims which follow thereafter.

EXAMPLES

A single-tower separation system with a configuration as illustrated in FIG. 1 was used. The rectification chamber has a height of 12 meters. The rectification plates contained a net-based structure. Lower pressure steam was used as the heating source. Operation parameters and the results are summarized in Table 1. The pressure of the rectification chamber was −0.098 MPa.

TABLE 1

| Temperature of the feed plate (° C.) | DMF (%) | Water (%) | Methanol (%) |
|---|---|---|---|
| 20 | 45-50 | 25-35 | 15-25 |
| 40-45 | 0.5-0.8 | 3-5 | 94-97 |
| 55-65 | 2-3 | 95-96 | 2-3 |
| 88 | 98.2-98.7 | 1.2-1.7 | 0.1 |

While the invention has been disclosed in its preferred forms, it will be apparent to those skilled in the art that many modifications, additions, and deletions can be made therein without departing from the spirit and scope of the invention and its equivalents as set forth in the following claims.

What is claimed is:

1. A method for isolating N,N-dimethylformamide ("DMF") from a composition comprising DMF, water, and methanol, comprising:
   introducing a composition comprising DMF, water, and methanol into a single-tower separation system, the single tower separation system comprising a lower section and an upper section, and the composition being introduced into the lower section;
   heating the composition;
   isolating DMF from the composition;
   drying the isolated DMF, whereby a substantially pure DMF is produced; and
   the heating of the composition comprising the steps of:
   reducing the pressure of the separation system by using a vacuum system;
   maintaining the temperatures of the lower section at about 25-45° C., whereby methanol is substantially removed from the composition; and
   maintaining the temperatures of the lower section at about 45-75° C., whereby water is substantially removed from the composition.

2. The method of claim 1, wherein the composition is heated using steam.

3. The method of claim 1, further comprising the step of:
   maintaining the temperatures of the lower section at about 60-95° C., whereby DMF is substantially removed from the composition.

4. The method of claim 1, wherein the substantially pure DMF comprises at least about 98-99% DMF.

5. A method for isolating DMF from a composition comprising DMF, water, and methanol, comprising:
   providing a single-tower separation system comprising a lower section and an upper section;
   introducing a composition comprising DMF, water, and methanol into the lower section of the single-tower separation system;
   reducing the pressure of the separation system by using a vacuum system;
   maintaining the temperatures of the lower section at about 25-45° C., whereby methanol is substantially removed from the composition;
   maintaining the temperatures of the lower section at about 45-75° C., whereby water is substantially removed from the composition;
   maintaining the temperatures of the lower section at about 60-95° C., whereby DMF is substantially removed from the composition; and
   drying the DMF, whereby a substantially pure DMF composition is produced.

6. The method of claim 5, wherein the temperature of the lower section is adjusted by using steam.

7. The method of claim 5, wherein the substantially pure DMF composition comprises at least about 98% DMF.

8. The method of claim 5, wherein the substantially pure DMF composition comprises at least about 99% DMF.

9. The method of claim 5, wherein the composition is dried by using a dehydration agent.

10. The method of claim 1, wherein the composition is dried by using a dehydration agent.

11. The method of claim 1, wherein the substantially pure DMF composition comprises at least about 98% DMF.

12. The method of claim 1, wherein the substantially pure DMF composition comprises at least about 99% DMF.

* * * * *